United States Patent
Dörr et al.

(10) Patent No.: US 8,980,966 B2
(45) Date of Patent: Mar. 17, 2015

(54) HYDROPHILIC ALIPHATIC POLYURETHANE FOAMS

(75) Inventors: Sebastian Dörr, Düsseldorf (DE); Meike Niesten, Köln (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 13/392,545

(22) PCT Filed: Aug. 26, 2010

(86) PCT No.: PCT/EP2010/062477
§ 371 (c)(1), (2), (4) Date: Feb. 27, 2012

(87) PCT Pub. No.: WO2011/023762
PCT Pub. Date: Mar. 3, 2011

(65) Prior Publication Data
US 2012/0157559 A1  Jun. 21, 2012

(30) Foreign Application Priority Data

Aug. 29, 2009 (EP) .................................... 09011102

(51) Int. Cl.
| | | |
|---|---|---|
| C08J 9/228 | (2006.01) | |
| C08G 18/72 | (2006.01) | |
| C08G 18/28 | (2006.01) | |
| A61L 15/26 | (2006.01) | |
| C08G 18/10 | (2006.01) | |
| C08G 18/12 | (2006.01) | |
| C08G 18/48 | (2006.01) | |
| C08G 18/73 | (2006.01) | |
| C08G 101/00 | (2006.01) | |

(52) U.S. Cl.
CPC .............. *C08G 18/283* (2013.01); *A61L 15/26* (2013.01); *C08G 18/10* (2013.01); *C08G 18/12* (2013.01); *C08G 18/4837* (2013.01); *C08G 18/73* (2013.01); *C08G 2101/00* (2013.01)
USPC ......................................................... 521/159

(58) Field of Classification Search
CPC .................................. C08G 18/72; C08J 9/228
See application file for complete search history.

(56) References Cited

U.S. PATENT DOCUMENTS

| | | |
|---|---|---|
| 3,889,417 A | 6/1975 | Wood et al. |
| 3,903,232 A | 9/1975 | Wood et al. |
| 5,064,653 A | 11/1991 | Sessions et al. |
| 5,065,752 A | 11/1991 | Sessions et al. |
| 5,296,518 A | 3/1994 | Grasel et al. |
| 6,191,179 B1 | 2/2001 | Scherzer et al. |
| 2009/0054542 A1* | 2/2009 | Schoenberger ............... 521/137 |
| 2009/0118387 A1 | 5/2009 | Sakakibara |
| 2011/0184080 A1 | 7/2011 | Schoenberger et al. |

FOREIGN PATENT DOCUMENTS

| | | |
|---|---|---|
| EP | 0299122 A1 | 1/1989 |
| EP | 0335669 | 10/1989 |
| EP | 949285 A1 | 10/1999 |
| EP | 08012372.2 | 7/2008 |
| GB | 1571730 A | 7/1980 |
| WO | WO-93/04101 A1 | 3/1993 |
| WO | WO-03/097727 A1 | 11/2003 |
| WO | WO-2004013215 A1 | 2/2004 |
| WO | WO-2011/006608 A1 | 1/2011 |

* cited by examiner

*Primary Examiner* — Randy Gulakowski
*Assistant Examiner* — Jeffrey Washville
(74) *Attorney, Agent, or Firm* — Drinker Biddle & Reath LLP

(57) ABSTRACT

The invention relates to hydrophilic aliphatic polyurethane foams obtained by reacting special prepolymers having a low monomer concentration and hydrophilic polyisocyanates in the presence of water. The absorptive properties make said polyurethane foams particularly suitable for producing wound dressings, cosmetic articles, or incontinence products.

14 Claims, No Drawings

HYDROPHILIC ALIPHATIC POLYURETHANE FOAMS

CROSS-REFERENCE TO RELATED APPLICATIONS

This application is a national stage application (under 35U.S.C. §371) of PCT/EP2010/062477, filed Aug. 26, 2010, which claims benefit of European application 09011102.2, filed Aug. 29, 2009, both of which are incorporated herein by reference in their entirety for all their useful purposes.

BACKGROUND

The invention relates to hydrophilic aliphatic polyurethane foams which are obtainable by reaction of specific low-monomer prepolymers and hydrophilic polyisocyanates in the presence of water. Owing to their absorptive properties, the polyurethane foams are particularly useful in the manufacture of wound dressings, cosmetic articles or incontinence products.

EP-A 949285 describes the reaction of polyisocyanates with primary diamines, low molecular weight polyols and high molecular weight polyols. This reaction does not preclude the possibility that appreciable portions of the isocyanate-reactive substances are not converted and are subsequently extractable from the hydrophilic foam.

GB 1571730 describes the reaction of high vapour pressure diisocyanates such as isophorone diisocyanate (IPDI) and bis(isocyanatocyclohexyl)methane (HMDI) with polyols. Again, unconverted components are left behind. Moreover, using free, non-derivatized diisocyanates is problematic from an occupational hygiene viewpoint. WO 2004013215 likewise utilizes volatile diisocyanates.

WO 2003/097727, U.S. Pat. Nos. 5,065,752 and 5,064,653 describe the foam-forming reaction of prepolymers in the presence of acrylamide-acrylic acid copolymers. These products are not chemically attached and are completely extractable, which is not desirable.

In U.S. Pat. Nos. 3,903,232 and 3,88,941, prepolymers are reacted with polyethers. Again, there is a risk of unattached polyols being produced. U.S. Pat. No. 5,296,518 similarly describes the reaction of prepolymers with polyethers wherein three different polyols are used, which calls the economics of this process into question. Furthermore, the process described therein is incapable of making certain that there are no low molecular weight isocyanates left in the mixture, which would not be desirable. The preparation of the prepolymers usually requires uneconomically long reaction times.

The as yet unpublished European patent application of application number 08012372.2 describes hydrophilic aliphatic polyurethane foams based on low-monomer prepolymers. However, the hydrophilicity of the resulting foams is limited. EP 08012372.2 does not disclose any polyurethane foams containing additional hydrophilic polyisocyanates.

Either the known polyurethane foams have an inadequate imbibition ability in respect of hydrophilic fluids, or they contain extractable substances that have to be classified as problematical with regard to their cell compatibility.

DESCRIPTION OF EMBODIMENTS

The present invention therefore has for its object to provide a process for preparing polyurethane foams which include but little by way of extractable constituents, are cell compatible, are capable of rapidly imbibing a large amount of hydrophilic fluids such as physiological saline or wound fluid, and are deformable such that they are able to optimally conform to the shape of a wound for example.

This object is achieved according to the invention by a process for preparing hydrophilic aliphatic polyurethane foams wherein compositions comprising A) isocyanate-functional prepolymers having a weight fraction of low molecular weight aliphatic diisocyanates having a molar mass of 140 to 278 g/mol of below 1.0% by weight based on the prepolymer, obtainable by reaction of
  A1) low molecular weight aliphatic diisocyanates having a molar mass of 140 to 278 g/mol with
  A2) di- to hexafunctional, preferably tri- to hexafunctional polyalkylene oxides having an OH number of 22.5 to 112 and an ethylene oxide content of 50 to 100 mol % based on the total amount of oxyalkylene groups present,
B) optionally heterocyclic 4-ring or 6-ring oligomers of low molecular weight aliphatic diisocyanates having a molar mass of 140 to 278 g/mol,
C) water,
D) optionally catalysts,
E) optionally $C_8$-$C_{22}$ monocarboxylic acids or their ammonium or alkali metal salts or $C_{12}$-$C_{44}$ dicarboxylic acids or their ammonium or alkali metal salts,
F) optionally surfactants, and
G) optionally mono- or polyhydric alcohols,
H) hydrophilic polyisocyanates obtainable by reaction of
  H1) low molecular weight aliphatic diisocyanates having a molar mass of 140 to 278 g/mol and/or polyisocyanates obtainable therefrom with an isocyanate functionality of 2 to 6, with
  H2) monofunctional polyalkylene oxides having an OH number of 10 to 250, and an ethylene oxide content of 50 to 100 mol % based on the total amount of oxyalkylene groups present, are provided, foamed and cured.

The prepolymers A) used preferably have a residual monomer content of below 0.5% by weight based on the prepolymer. This content can be achieved through appropriately selected use quantities of diisocyanates A1) and polyalkylene oxides A2). However, it is preferable to use diisocyanate A1) in excess and subsequent, preferably distillative, removal of unconverted monomers.

The isocyanate-functional prepolymers A) are typically prepared by adjusting the ratio of polyalkylene oxides A2) to low molecular weight aliphatic diisocyanates A1) such that for every 1 mol of OH groups of polyalkylene oxides A2) there are from 2 to 20 mol, preferably from 2 to 10 mol and more preferably from 5 to 10 mol of NCO groups of low molecular weight aliphatic diisocyanate A1).

The reaction can take place in the presence of urethanization catalysts such as tin compounds, zinc compounds, amines, guanidines or amidines, or in the presence of allophanatization catalysts such as zinc compounds.

The reaction temperature is typically in the range from 25 to 140° C., preferably in the range from 60 to 100° C.

When excess isocyanate was used, the excess of low molecular weight aliphatic diisocyanate is subsequently preferably removed by thin film distillation.

Before, during and after the reaction or distillative removal of the excess diisocyanate, acidic or alkylating stabilizers, such as benzoyl chloride, isophthaloyl chloride, methyl tosylate, chloropropionic acid, HCl or antioxidants, such as di-tert-butylcresol or tocopherol can be added.

The NCO content of the isocyanate-functional prepolymers A) is preferably in the range from 1.5% to 4.5% by weight, more preferably in the range from 1.5% to 3.5% by weight and most preferably in the range from 1.5% to 3.0% by weight.

Examples of low molecular weight aliphatic diisocyanates of component A1) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylylene diisocyanate, tetramethylxylylene diisocyanate, norbornane diisocyanate, cyclohexane diisocyanate or diisocyanatododecane, of which hexamethylene diisocyanate (HDI), isophorone diisocyanate (IPDI), butylene diisocyanate (BDI) and bis(isocyanatocyclohexyl)methane (HMDI) are preferred. BDI, HDI, IPDI are particularly preferred and hexamethylene diisocyanate and isophorone diisocyanate are very particularly preferred.

Polyalkylene oxides of component A2) are preferably copolymers of ethylene oxide and propylene oxide having an ethylene oxide content, based on the total amount of oxyalkylene groups present, of 50 to 100 mol %, preferably of 60 to 85 mol %, and started on polyols or amines. Suitable starters of this kind are glycerol, trimethylolpropane (TMP), sorbitol, pentaerythritol, triethanolamine, ammonia or ethylenediamine.

The number average molecular weight of the polyalkylene oxides of component A2) is typically in the range from 1000 to 15 000 g/mol and preferably in the range from 3000 to 8500 g/mol.

The polyalkylene oxides of component A2) further have OH functionalities of 2 to 6, preferably of 3 to 6 and more preferably of 3 to 4.

Optional compounds of component B) are heterocyclic 4-ring or 6-ring oligomers of low molecular weight aliphatic diisocyanates having a molar mass of 140 to 278 g/mol such as isocyanurates, iminooxadiazinediones or uretdiones of the aforementioned low molecular weight aliphatic diisocyanates. Heterocyclic 4-ring oligomers such as uretdiones are preferred.

The increased isocyanate group content due to the use of component B) provides better foaming, since more $CO_2$ is formed in the isocyanate-water reaction.

The water used as component C) can be used as such, as water of crystallization of a salt, as solution in a dipolar aprotic solvent or else as an emulsion. Preferably, the water is used as such or in a dipolar aprotic solvent. It is very particularly preferred to use water as such.

To speed urethane formation, component D) may utilize catalysts. The catalysts in question are typically compounds with which a person skilled in the art is familiar from polyurethane technology. Preference here is given to compounds from the group consisting of catalytically active metals, amines, amidines and guanidines. Specific examples are dibutyltin dilaurate (DBTL), tin acetate, 1,8-diazabicyclo[5.4.0]undecene-7 (DBU), 1,5-diazabicyclo[4.3.0]nonene-5 (DBN), 1,4-diazabicyclo[3.3.0]octene-4 (DBO), N-ethylmorpholine (NEM), triethylenediamine (DABCO), pentamethylguanidine (PMG), tetramethylguanidine (TMG), cyclotetramethylguanidine (TMGC), n-decyltetramethylguanidine (TMGD), n-dodecyltetramethylguanidine (TMGDO), dimethylaminoethyltetramethylguanidine (TMGN), 1,1,4,4,5,5-hexamethylisobiguanidine (HMIB), phenyltetramethylguanidine (TMGP) and hexamethyleneoctamethylbiguanidine (HOBG).

Preference is given to the use of amines, amidines, guanidines or mixtures thereof as catalysts of component D). Preference is also given to the use of 1,8-diazabicyclo[5.4.0]undecene-7 (DBU).

In a particularly preferred embodiment of the invention catalysts are dispensed with completely.

Component E) may optionally utilize ammonium and alkali metal salts of $C_8$-$C_{22}$ monocarboxylates or their free carboxylic acids or $C_{12}$-$C_{44}$ dicarboxylates or their free dicarboxylic acids, preferably potassium or sodium salts of $C_8$-$C_{22}$ monocarboxylates or $C_{12}$-$C_{44}$ dicarboxylates and more preferably sodium salts of $C_8$-$C_{22}$ monocarboxylates.

Examples of suitable compounds of component E) are the ammonium, sodium, lithium or potassium salts of ethylhexanoic acid, octanoic acid, decanoic acid, dodecanoic acid, palmitic acid, stearic acid, the octadecenoic acids, the octadecadienoic acids, the octadecatrienoic acids, isostearic acid, erucic acid, abietic acid and hydrogenation products thereof. Examples of $C_{12}$-$C_{44}$ dicarboxylic acids and the ammonium and alkali metal salts derived therefrom are dodecanedioic acid, dodecenylsuccinic acid, tetradecenylsuccinic acid, hexadecenylsuccinic acid, octadecenylsuccinic acid, $C_{36}$ and $C_{44}$ dimer fatty acids and hydrogenation products thereof and also the corresponding ammonium, sodium, lithium or potassium salts of these dicarboxylic acids.

Compounds of component F) can be used to improve foam formation, foam stability or the properties of the resulting polyurethane foam, in which case such additives can in principle be any known anionic, cationic, amphoteric and nonionic surfactants and also mixtures thereof. Preference is given to using alkylpolyglycosides, EO-PO block copolymers, alkyl or aryl alkoxylates, siloxane alkoxylates, esters of sulphosuccinic acid and/or alkali or alkaline earth metal alkanoates. Particular preference is given to using EO-PO block copolymers. Preferably, the EO-PO block copolymers are solely used as component F).

In addition, compounds of component G) can be used to improve the foam properties of the resulting polyurethane foam. These compounds comprise in principle any mono- and polyhydric alcohols known per se to a person skilled in the art, and also mixtures thereof. These are mono- or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyether diols and polyester diols.

The hydrophilic polyisocyanates H) are typically prepared by adjusting the ratio of monofunctional polyalkylene oxides H2) to low molecular weight aliphatic diisocyanates H1) such that for every 1 mol of OH groups of the monofunctional polyalkylene oxides there are from 1.25 to 15 mol, preferably from 2 to 10 mol and more preferably from 2 to 6 mol of NCO groups of low molecular weight aliphatic diisocyanate H1). This is followed by the allophanatization/biuretization and/or isocyanurate formation/uretdione formation. When the polyalkylene oxides H2) become bonded to the aliphatic diisocyanates He via urethane groups, it is preferably an allophanatization which takes place subsequently. It is further preferable for isocyanurate structural units to be formed.

An alternative way to prepare the hydrophilic polyisocyanates H) typically involves reacting 1 mol of OH groups of the monofunctional polyalkylene oxide component H2) with 1.25 to 15 mol, preferably with 2 to 10 mol and more preferably 2 to 6 mol of NCO groups of a polyisocyanate H1) having an isocyanate functionality of 2 to 6, based on aliphatic diisocyanates. Exemplary of such polyisocyanates H1)

are biuret structures, isocyanurates/uretdiones based on aliphatic diisocyanates. The polyisocyanate H1) and the polyalkylene oxide H2) are preferably linked together via a urethane group or a urea group, although particularly the linking via urethane groups is preferable.

The reaction can be carried out in the presence of urethanization catalysts such as tin compounds, zinc compounds, amines, guanidines or amidines, or in the presence of allophanatization catalysts such as zinc compounds.

The reaction temperature is typically in the range from 25 to 140° C. and preferably in the range from 60 to 100° C.

When excess low molecular weight diisocyanate was used, excess low molecular weight aliphatic diisocyanate is subsequently removed, preferably by thin film distillation.

Before, during and after the reaction or distillative removal of excess diisocyanate, acidic or alkylating stabilizers, such as benzoyl chloride, isophthaloyl chloride, methyl tosylate, chloropropionic acid, HCl or antioxidants, such as di-tert-butylcresol or tocopherol can be added.

The NCO content of hydrophilic polyisocyanates H) is preferably in the range from 0.3% to 20% by weight, more preferably in the range from 2% to 10% by weight and most preferably in the range from 3% to 6% by weight.

Examples of low molecular weight aliphatic diisocyanates of component H1) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, of which hexamethylene diisocyanate (HDI), isophorone diisocyanate (IPDI), butylene diisocyanate (BDI) and bis(isocyanatocyclohexyl)methane (HMDI) are preferable. BDI, MI and IPDI are more preferable and hexamethylene diisocyanate and isophorone diisocyanate are most preferable.

Examples of comparatively high molecular weight polyisocyanates H2) are polyisocyanates having an isocyanate functionality of 2 to 6 with isocyanurate, urethane, allophanate, biuret, iminooxadiazinetrione, oxadiazinetrione and/or uretdione groups based on the aliphatic and/or cycloaliphatic diisocyanates mentioned in the preceding section.

Preference for use as component H2) is given to comparatively high molecular weight compounds with biuret, iminooxadiazinedione, isocyanurate and/or uretdione groups based on hexamethylene diisocyanate, isophorone diisocyanate and/or 4,4'-diisocyanatodicyclohexylmethane. Isocyanurates further are preferable. Structures based on hexamethylene diisocyanate are most preferable.

The monofunctional polyalkylene oxides H2) have an OH number of 15 to 250, preferably of 28 to 112, and an ethylene oxide content of 50 to 100 mol %, preferably of 60 to 100 mol %, based on the total amount of oxyalkylene groups present.

Monofunctional polyalkylene oxides for the purposes of the invention are compounds having just one isocyanate-reactive group, i.e., a group capable of reacting with an NCO group.

Preparing polyalkylene oxides H2) by alkoxylating suitable starter molecules is literature known (e.g., Ullmanns Encyclopädie der technischen Chemie, 4th edition, volume 19, Verlag Chemie, Weinheim pp. 31-38). Suitable starter molecules are especially saturated monoalcohols such as methanol, ethanol, n-propanol, isopropanol, n-butanol, isobutanol, sec-butanol, diethylene glycol monobutyl ether and also aromatic alcohols such as phenol or monoamines such as diethylamine. Preferred starter molecules are saturated monoalcohols of the aforementioned kind. It is particularly preferable to use diethylene glycol monobutyl ether or n-butanol as starter molecules.

The number average molecular weights of monofunctional polyalkylene oxides H2) are typically in the range from 220 to 3700 g/mol and preferably in the range from 500 to 2800 g/mol.

The monofunctional polyalkylene oxides H2) preferably have an OH group as isocyanate-reactive group.

Components A) to H) are typically used in the following amounts:
  100 parts by weight of isocyanate-functional prepolymers A)
  0 to 30 parts by weight of heterocyclic oligomers B)
  0.1 to 200 parts by weight of water C)
  0 to 1 part by weight of catalysts D)
  0 to 5 parts by weight of $C_8$-$C_{12}$-monocarboxylic acids or their ammonium or alkali metal salts or $C_{12}$-$C_{44}$-dicarboxylic acids or their ammonium or alkali metal salts E)
  0 to 10 parts by weight of surfactants F)
  0 to 20 parts by weight of alcohols G)
  5 to 250 parts by weight of hydrophilic polyisocyanate component H)

Components A) to H) are preferably used in the following amounts:
  100 parts by weight of isocyanate-functional prepolymers A)
  1 to 30 parts by weight of heterocyclic oligomers B)
  0.1 to 100 parts by weight of water C)
  0 to 1 part by weight of catalysts D)
  0.01 to 5 parts by weight of $C_8$-$C_{12}$-monocarboxylic acids or their ammonium or alkali metal salts or $C_{12}$-$C_{44}$-dicarboxylic acids or their ammonium or alkali metal salts E)
  0 to 5 parts by weight of surfactants F)
  0 to 10 parts by weight of alcohols G)
  10 to 100 parts by weight of hydrophilic polyisocyanates H)

Components A) to H) are more preferably used in the following amounts:
  100 parts by weight of isocyanate-functional prepolymers A)
  5 to 15 parts by weight of heterocyclic oligomers B)
  1 to 60 parts by weight of water C)
  0 to 0.5 part by weight of catalysts D)
  0.1 to 1 part by weight of $C_8$-$C_{12}$-monocarboxylic acids or their ammonium or alkali metal salts or $C_{12}$-$C_{44}$-dicarboxylic acids or their ammonium or alkali metal salts E)
  0 part by weight of surfactants F)
  0 part by weight of alcohols G)
  20 to 80 parts by weight of hydrophilic polyisocyanates H)

The hydrophilic aliphatic polyurethane foams according to the invention are prepared by mixing the components A), C), H) and optionally B), D), E), F), G) in any order, foaming the mixture and curing preferably by chemical crosslinking. The components A), B) and H) are preferably premixed with each other. The carboxylates E) optionally to be used and, if used, the surfactants F) are preferably added to the reaction mixture in the form of aqueous solutions.

Foaming can in principle be effected by means of the carbon dioxide formed in the course of the reaction of the isocyanate groups with water, but the use of further blowing agents is likewise possible. It is thus also possible in principle to use blowing agents from the class of the hydrocarbons such as $C_3$-$C_6$ alkanes, for example butanes, n-pentane, isopentane, cyclopentane, hexanes or the like, or halogenated hydrocarbons such as dichloromethane, dichloromono-fluoromethane, chlorodifluoroethanes, 1,1-dichloro-2,2,2-trifluoroethane, 2,2-dichloro-2-fluoro-ethane, particularly chlorine-free hydrofluoro carbons such as difluoromethane, trifluoromethane, difluoroethane, 1,1,1,2-tetrafluoroethane, tetrafluoroethane (R 134 or R 134a), 1,1,1,3,3-penta-fluoropropane (R 245 fa), 1,1,1,3,3,3-hexafluoropropane (R 256), 1,1,1,3,3-pentafluorobutane (R 365 mfc), heptafluoropropane, or else sulphur hexafluoride. Mixtures of these blowing agents can also be used.

Subsequent curing typically takes place at room temperature.

The present invention further provides the compositions according to the invention and also the hydrophilic aliphatic polyurethane foams obtainable therefrom.

The present invention further provides the polyurethane foams prepared by the process of the present invention and also for the use of the hydrophilic aliphatic polyurethane foams as constituent of a wound dressing, of a cosmetic article or of an incontinence product.

The polyurethane foams have a porous, at least partially open-cell structure having intercommunicating cells. The density of the polyurethane foams is typically in the range from 0.01 to 0.5 g/cm$^3$ (determined according to DIN 53420).

Physiological saline absorbence of the polyurethane foams is typically 25 to 150 g per 100 cm$^2$ in the case of a 5 mm thick foam. The measurement is carried out here according to the following method: (determination according to DIN EN 13726-1 Part 3.2).

Compared with other hydrophilic foams, the polyurethane foams according to the invention provide a very high physiological saline absorbance even without the use of superabsorbent polymers. However, the incorporation of superabsorbent is also possible with the polyurethane foams according to the invention, as will be appreciated.

The polyurethane foams have good mechanical strength and high elasticity. Tensile strength is typically greater than 40 kPa, breaking extension greater than 30% and rebound elasticity greater than 60% (determined according to DIN 53504, DIN 53455, DIN EN ISO 3386-1).

After they have been prepared, the polyurethane foams can be made into sheetlike materials in a conventional manner and then can be used, for example, as a constituent of a wound dressing, of a cosmetic article or of an incontinence product. Generally, to this end, slab foams are cut to the desired thickness by common methods by means of which sheetlike materials having a thickness of typically from 10 μm to 5 cm, preferably from 0.1 mm to 1 cm, more preferably from 0.1 mm to 6 mm and most preferably from 0.2 mm to 6 mm, are to be obtained.

However, the sheetlike materials described can also be obtained directly using suitable casting techniques, by application and foaming of the composition according to the invention onto a substrate, for example an optionally pretreated paper or textile.

In a preferable version, a mixture of the starting materials is for this purpose, as described in the as yet unpublished European application numbered 09009202.4, applied to a substrate by blade coating whereupon, subsequent to the blade coating, the foaming up takes place. The gap height of the blade coater is generally in the range from 0.2 to 20 mm, preferably in the range from 0.5 to 5 and more preferably in the range from 0.8 to 2 mm. The film width of the blade coater to be used can be adapted to the particular purpose of use. Examples are film widths between 10 and 5000 mm and preferably between 20 and 2000 mm.

The polyurethane foams generally contain a but minimal water-extractable fraction of not more than 2% by weight and preferably of not more than 1% by weight; i.e., they contain only very small amounts of constituents which are not chemically bound.

The polyurethane foams may moreover be adhered to or laminated or coated with further materials, for example materials based on hydrogels, (semi)permeable films, foam films, coatings, hydrocolloids or other foams.

The polyurethane foams according to the invention are particularly useful in the manufacture of wound dressings. In these dressings, the polyurethane foams can be in direct or indirect contact with the wound. Preferably, however, the polyurethane foams are used in direct contact with the wound in order that optimum absorbence of wound fluid may be ensured for example. The polyurethane foams exhibit no cytotoxicity (determined according to ISO 10993-5 and ISO 10993-12).

The polyurethane foams which are used as wound dressing have to be additionally sterilized in a further operation. The sterilization is effected using processes known per se to one skilled in the art, wherein sterilization is effected by thermal treatment, chemical substances such as ethylene oxide or irradiation, for example by gamma irradiation. Irradiation here may be carried out under protective gas atmosphere, where appropriate. The polyurethane foams according to the invention have the immense advantage of not discolouring on irradiation, in particular on irradiation with gamma rays.

It is likewise possible to add, incorporate or coat antimicrobially or biologically active components which have a positive effect for example in relation to wound healing and the avoidance of germ loads.

EXAMPLES

Unless stated otherwise, all percentages are by weight. Solids contents were determined according to DIN-EN ISO 3251. Viscosities were determined at 23° C. to DIN 53019. NCO contents were determined volumetrically in accordance with DIN-EN ISO 11909.

The blade coater used was a Zehntner ZUA 2000 universal applicator having a film width of 200 mm and a gap height adjustable from 0 to 3 mm (from Zehntner GmbH, Sissach, Switzerland).

Substances and Abbreviations Used:

Desmodur® N 3400: aliphatic polyisocyanate (HDI uretdione), NCO content 21.8%, Bayer MaterialScience AG, Leverkusen, Germany Desmodur® N 3300: aliphatic polyisocyanate (HDI isocyanurate), NCO content 21.8%, Bayer MaterialScience AG, Leverkusen, Germany Example 1

Preparation of Polyurethane Prepolymer 1 (Building Block A)

A mixture of 1000 g HDI and 1 g of benzoyl chloride was admixed at 80° C. during 3 h with 1000 g of a polyalkylene oxide having a molar mass of 4680 g/mol started on glycerol, an ethylene oxide weight fraction of 72% and a propylene oxide weight fraction of 28% and dried beforehand at 100° C. during 6 h at a pressure of 0.1 mbar, by dropwise addition and subsequently stirred for 12 h. Excess HDI was removed by thin film distillation at 130° C. and 0.1 mbar, and the non-volatile constituents were stabilized with 1 g of chloropropionic acid. This gave a prepolymer having an NCO content of 2.77% and a viscosity of 3500 mPas.

Example 2

Preparation of Polyurethane Prepolymer 2 (Building Block A)

A mixture of 200g HDI, 1 g of benzoyl chloride and 1 g of methyl tosylate was admixed at 80° C. during 2 h with 400 g of a polyalkylene oxide having a molar mass of 5800 g/mol started on glycerol, an ethylene oxide content of 80% and a propylene oxide content of 20% and dried beforehand at 100° C. during 6 h at a pressure of 0.1 mbar, by dropwise addition and subsequently stirred for 12 h. Excess HDI was removed by thin film distillation at 130° C. and 0.1 mbar. This gave a prepolymer having an NCO content of 2.31% and a viscosity of 6070 mPas.

Example 3

Preparation of Polyurethane Prepolymer 3 (Building Block A)

A mixture of 1440g HDI and 4 g of benzoyl chloride was admixed at 80° C. during 2 h with 2880 g of a polyalkylene oxide having a molar mass of 4680 g/mol started on glycerol, an ethylene oxide weight fraction of 72% and a propylene oxide weight fraction of 28% and dried beforehand at 100° C. during 6 h at a pressure of 0.1 mbar, by dropwise addition and subsequently stirred for 1 h. Excess HDI was removed by thin film distillation at 130° C. and 0.1 mbar. This gave a prepolymer having an NCO content of 2.11% and a viscosity of 3780 mPas.

Example 4

Preparation of Polyurethane Prepolymer 4 (Building Block A)

A mixture of 200 g HDI, 1 g of benzoyl chloride and 1 g of methyl tosylate was admixed at 80° C. during 2 h with 400 g of a polyalkylene oxide having a molar mass of 5800 g/mol started on glycerol, an ethylene oxide content of 80% and a propylene oxide content of 20% and dried beforehand at 100° C. during 6 h at a pressure of 0.1 mbar, by dropwise addition and subsequently stirred for 12 h. Excess IPDI was removed by thin film distillation at 130° C. and 0.1 mbar. This gave a prepolymer having an NCO content of 2.36% and a viscosity of 8800 mPas.

Example 5

Preparation of hydrophilic polyisocyanates (building block H)

A mixture of 282.5 g of Desmodur N 3300 and 843.8 g of a hydroxyl-monofunctional polyether based on ethylene oxide/propylene oxide (having an ethylene oxide content of 80 mol based on total amount of oxyalkylene groups present), number average molecular weight 2250 g/mol (OH number 25 mg KOH/g) was stirred in a glass apparatus at 80° C. until the titrimetrically determined NCO group content was constant. This gave a liquid having an NCO content of 4.04% and a viscosity of 3330 mPas.

Example 6

Preparation of Hydrophilic Polyisocyanates (Building Block H)

A mixture of 780.0 g of Desmodur N 3300 and 500.0 g of a hydroxyl-monofunctional polyether based on ethylene oxide, number average molecular weight 500 g/mol (OH number 112 mg KOH/g) was stirred in a glass apparatus at 80° C. until the titrimetrically determined NCO group content was constant. This gave a liquid having an NCO content of 9.79% and a viscosity of 2510 mPas.

Example 7

Preparation of Hydrophilic Polyisocyanates (Building Block H)

A mixture of 214.5 g of Desmodur N 3300 and 990.0 g of a hydroxyl-monofunctional polyether based on ethylene oxide/propylene oxide (having an ethylene oxide content of 80 mol based on total amount of oxyalkylene groups present), number average molecular weight 2250 g/mol (OH number 25 mg KOH/g) was stirred in a glass apparatus at 80° C. until the titrimetrically determined NCO group content was constant. This gave a liquid having an NCO content of 2.39%.

Example 8

Preparation of Hydrophilic Polyisocyanates (Building Block H)

A mixture of 84,71 g of Desmodur N 3300 and 781.9 g of a hydroxyl-monofunctional polyether based on ethylene oxide/propylene oxide (having an ethylene oxide content of 80 mol based on total amount of oxyalkylene groups present), number average molecular weight 2250 g/mol (OH number 25 mg KOH/g) was stirred in a glass apparatus at 80° C. until the titrimetrically determined NCO group content was constant. This gave a liquid having an NCO content of 0.29%.

Preparation of Foamed Materials

The two isocyanate components were homogenized for 15 seconds using a stirrer speed of 1200 rpm, then the further components were weighed in, stirring was continued for a further 10 seconds and the mixture was applied to siliconized release paper using a blade coater (gap height 1.5 mm). The oligomer, if used, was Desmodur® N 3400 in each case; as carboxylate, a 5% solution of sodium oleate in water. Extra water added is reported separately.

| Component [g] | Foam example | | | | | | | | |
|---|---|---|---|---|---|---|---|---|---|
| | 1* | 2 | | 4 | 5 | 6 | 7 | 8 | 9 |
| prepolymer (building block A) from Ex. 1 | 75 g | 60 g | 45 g | 45 g | 30 g | 45 g | 30 g | 45 g | 30 g |
| oligomer | 8.33 g | 8.3 g | 0 | 8.3 g | 8.3 g | 0 g | 0 g | 0 | 0 |
| water (building block C) | 3.35 g | 3.35 g | 3.5 g | 3.5 g | 3.5 g | 3.35 g | 45 g | 3.35 g | 3.35 g |
| hydrophilic PIC (building block H) | 0 | 15 g Ex. 5 | 45 g Ex. 5 | 30 g Ex. 5 | 45 g Ex. 5 | 30 g Ex. 6 | 45 g Ex. 6 | 30 g Ex. 7 | 45 g Ex. 7 |

-continued

| Component [g] | Foam example | | | | | | | |
|---|---|---|---|---|---|---|---|---|
| | 1* | 2 | 4 | 5 | 6 | 7 | 8 | 9 |
| sodium oleate (building block E) as 5% by weight of solution in water | 8.30 g | 8.3 g | 8.2 g | 8.2 g | 8.2 g | 8.3 g | 8.3 g | 8.3 g | 8.3 g |
| raw density [g/1000 cm$^3$] | 174 | 151 | 247 | 141 | 125 | 151 | 120 | 147 | 296 |
| foam thickness [mm] | 3.8 | 4.9 | 3.4 | 5.8 | 6.7 | 6.0 | 7.8 | 6.2 | 2.2 |
| water imbibition [g/100 cm$^2$] | 31.4 | 83 | 86 | 106 | 142 | 85 | 98 | 104 | 53 |
| water imbibition [g/100 cm$^2$] per mm foam thickness | 8.3 | 16.9 | 25.3 | 18.3 | 21.2 | 14.2 | 12.6 | 16.8 | 17.9 | oligomer (if present): Desmodur N 3400
*comparative example: foam without invention-essential component H)

Inventive Examples 2-9 were foams having a very uniform, fine porous structure and pleasant, soft haptics.

As these examples and the comparative example illustrate, the inventive components H) constitute a crucial additive in the foam production described: without this component it is not possible to achieve a very high water imbibition. This is surprising since component A) already contains a very high proportion of hydrophilic polyethers. It was unforeseeable that an improvement occurs here on addition of building blocks of component H). Nor was the advantageous haptic assessment of foams according to the invention foreseeable.

The invention claimed is:

1. Process for preparing hydrophilic aliphatic polyurethane foams consisting essentially of mixing
   A) isocyanate-functional prepolymers having a weight fraction of low molecular weight aliphatic diisocyanates having a molar mass of 140 to 278 g/mol of below 1.0% by weight based on the prepolymer, obtainable by reaction of
      A1) low molecular weight aliphatic diisocyanates having a molar mass of 140 to 278 g/mol with
      A2) di- to hexafunctional polyalkylene oxides having an OH number of 22.5 to 112 mg KOH/g and an ethylene oxide content of 50 to 100 mol % based on the total amount of oxyalkylene groups present,
   with
   B) optionally heterocyclic 4-ring or 6-ring oligomers of low molecular weight aliphatic diisocyanates having a molar mass of 140 to 278 g/mol,
   C) water,
   D) optionally catalysts,
   E) optionally C$_8$-C$_{22}$ monocarboxylic acids or their ammonium or alkali metal salts or C$_{12}$-C$_{44}$ dicarboxylic acids or their ammonium or alkali metal salts,
   F) optionally surfactants, and
   G) optionally mono- or polyhydric alcohols, and
   H) hydrophilic polyisocyanates obtainable by reaction of
      H1) low molecular weight aliphatic diisocyanates having a molar mass of 140 to 278 g/mol and/or polyisocyanates obtainable therefrom with an isocyanate functionality of 2 to 6, with
      H2) monofunctional polyalkylene oxides having an OH number of 10 to 250, and an ethylene oxide content of 50 to 100 mol % based on the total amount of oxyalkylene groups present,
   to form a mixture,
   foaming the mixture by means of carbon dioxide formed in the course of the reaction of the isocyanate groups of the prepolymers A) with water C) and optionally by the use of further blowing agents and
   curing the mixture by chemical crosslinking.

2. The process according to claim 1, wherein the monofunctional polyalkylene oxide H2) has an OH number of 20 to 112.

3. The process according to claim 1, wherein the monofunctional polyalkylene oxide H2) has an ethylene oxide content of 60 to 90 mol % based on the total amount of oxyalkylene groups present.

4. The process according to claim 1, wherein the NCO content of the isocyanate-functional prepolymer A) is 1.5% to 3.0% by weight.

5. The process according to claim 1, wherein A1) consists of an hexamethylene diisocyanate (HDI), an isophorone diisocyanate (IPDI) or mixtures thereof.

6. The process according to claim 1, wherein the polyalkylene oxide A2) comprises a copolymer of ethylene oxide and propylene oxide having an ethylene oxide content, based on the total amount of oxyalkylene groups present, of 60 to 85 mol % and started on polyols or amines.

7. The process according to claim 1, wherein the polyalkylene oxide of component A2) has a number average molecular weight of 3000 to 8500 g/mol.

8. The process according to claim 1, wherein the polyalkylene oxide of A2) has OH functionalities of 3 to 4.

9. The process according to claim 1, wherein component B) is present and comprises an heterocyclic 4-ring oligomer.

10. The process according to claim 1, wherein the catalyst D) comprises a metal salt, an amine, an amidine and/or a guanidine.

11. The process according to claim 1, wherein components A) to H) are used in the following amounts:
   100 parts by weight of isocyanate-functional prepolymers A)
   0 to 30 parts by weight of heterocyclic oligomers B)
   0.1 to 200 parts by weight of water C)
   0 to 1 part by weight of catalysts D)
   0 to 5 parts by weight of C$_8$-C$_{12}$ monocarboxylic acids or their ammonium or alkali metal salts or C$_{12}$-C$_{44}$ dicarboxylic acids or their ammonium or alkali metal salts E),
   0 to 10 parts by weight of surfactants F)
   0 to 20 parts by weight of alcohols G)
   5 to 250 parts by weight of hydrophilic polyisocyanates H).

12. A polyurethane foam obtained by the process according to claim 1.

13. A wound dressing, cosmetic article or incontinence product obtained from the polyurethane foam according to claim 12.

14. The process according to claim 1, wherein components A) to H) are used in the following amounts:

- 100 parts by weight of isocyanate-functional prepolymers A)
- 0 to 30 parts by weight of heterocyclic oligomers B)
- 1 to 60 parts by weight of water C)
- 0 to 1 part by weight of catalysts D)
- 0 to 5 parts by weight of $C_8$-$C_{12}$ monocarboxylic acids or their ammonium or alkali metal salts or $C_{12}$-$C_{44}$ dicarboxylic acids or their ammonium or alkali metal salts E),
- 0 to 10 parts by weight of surfactants F)
- 0 to 20 parts by weight of alcohols G)
- 5 to 250 parts by weight of hydrophilic polyisocyanates H).

* * * * *